(12) United States Patent
Babusik et al.

(10) Patent No.: US 9,220,645 B2
(45) Date of Patent: Dec. 29, 2015

(54) ABSORBENT ARTICLE WITH EMBOSSING

(75) Inventors: Kimberly H. Babusik, Mullica Hill, NJ (US); Michael J. Naughton, Birdsboro, PA (US); Audra Niszczak, East Norriton, PA (US)

(73) Assignee: FIRST QUALITY RETAIL SERVICES, LLC, Great Neck, NY (US)

( * ) Notice: Subject to any disclaimer, the term of this patent is extended or adjusted under 35 U.S.C. 154(b) by 696 days.

(21) Appl. No.: 11/805,641

(22) Filed: May 24, 2007

(65) Prior Publication Data

US 2008/0004581 A1 Jan. 3, 2008

Related U.S. Application Data

(60) Provisional application No. 60/817,985, filed on Jun. 30, 2006.

(51) Int. Cl.
| | |
|---|---|
| *A61F 13/15* | (2006.01) |
| *A61F 13/537* | (2006.01) |
| *A61F 13/533* | (2006.01) |

(52) U.S. Cl.
CPC ........... *A61F 13/5376* (2013.01); *A61F 13/533* (2013.01); *A61F 13/53747* (2013.01); *A61F 2013/15487* (2013.01); *A61F 2013/53782* (2013.01)

(58) Field of Classification Search
CPC ....... A61F 13/15; A61F 13/47; A61F 13/511; A61F 13/536
USPC .................................. 604/367–369, 378–380
See application file for complete search history.

(56) References Cited

U.S. PATENT DOCUMENTS

| | | | | |
|---|---|---|---|---|
| 6,068,620 | A * | 5/2000 | Chmielewski | 604/378 |
| 6,210,385 | B1 * | 4/2001 | Mizutani | 604/385.01 |
| 2003/0093050 | A1 * | 5/2003 | Baker | 604/378 |

FOREIGN PATENT DOCUMENTS

EP 1330995 A2 7/2003

* cited by examiner

*Primary Examiner* — Melanie Hand
(74) *Attorney, Agent, or Firm* — Kenneth George; Benjamin Halpern

(57) ABSTRACT

The present invention describes a novel absorbent core for the absorbent article in which the top surface of the core is embossed in a pattern that is made from curves rather than straight lines or polygons. In a preferred embodiment, the top surface is embossed with a pattern made by circles with spacing between consecutive circles. The novel article is not only less rigid and smoother on the body surface, but also exhibits better absorptive capacity. Various other embodiments are described and are within the scope of the invention.

20 Claims, 7 Drawing Sheets

ABSORBENT ARTICLE WITH EMBOSSING

CROSS-REFERENCE TO RELATED APPLICATIONS

This application claims the benefit of U.S. Provisional Application Ser. No. 60/817,985, filed Jun. 30, 2006, the disclosure of which is incorporated herein.

BACKGROUND OF THE INVENTION

According to the present invention, an absorbent article is described having improved absorbency characteristics and a method of making the same. More particularly, the present invention describes an absorbent core of an airlaid material having an embossed pattern on its top surface. The use of absorbent articles has become quite prevalent in today's world.

They have been improved and modified so as to have varying shapes, sizes, and characteristics as per the particular application. For example, baby diapers are large smooth articles with high absorbent capacity, thus making it possible for the baby to wear the article for a long period of time. At the same time, sanitary pads or pantiliners worn by females are relatively small articles that are not noticeable from the outside, thus avoiding the wearer any embarrassment.

One of the areas in this field where a significant amount of research has been done is in the construction of the absorbent core of the article. The absorbent core, generally, absorbs and retains body fluids so that they can be easily disposed of.

In order to improve the absorbency, retention and other desired properties of the core, various natural and synthetic materials have been introduced in its construction. The objective being that the core should be an optimized result of the weight of its constituents and the absorbency and retention it offers.

In the most simplistic construction of an absorbent article, this core is disposed between a liquid permeable body facing top sheet and a liquid impermeable garment facing back sheet. However since this portion forms the bulk of the article, it contributes significantly to the comfort factor when the article is worn. More so, when the article is worn, this portion is disposed in the crotch region of the wearer, where even a slight amount of discomfort is least desirable.

Furthermore, since a combination of natural and man made fibers and other materials are used in making an efficient absorbent core, it is important to bind the materials together so as to provide uniformity as well as strength. In order to provide the desired amount of strength, softness, as well as looks, one common approach in the field is to bind the absorbent core fibers by embossing the core.

The embossing also achieves a combination of high density embossed regions and/or lines along with low-density non-embossed regions. This combination creates lines, or depressions, in the absorbent core that aid in an efficient absorption of the body-released fluids.

U.S. Pat. No. 4,518,451, issued to Luceri et al., discloses an embossed pantiliner where the body facing side is imposed with a relatively deep pattern of depressed areas, and the longitudinal edges are imposed with a pattern of relatively shallow depressed areas. This results in a pantiliner that has aesthetically effective embossing while providing comfortable longitudinal edges.

U.S. Pat. No. 4,623,340, issued to Luceri, discloses an absorbent pantiliner provided with a pattern of depressed areas. The outer cover of the pantiliner is made from a relatively light opaque sheet material and the interior layer is at least partially thermoplastic and relatively dark colored. When the cover is embossed, the depressed areas appear darker than the un-embossed areas.

U.S. Pat. No. 5,514,104 issued to Cole et al., discloses an absorbent article comprising an absorbent core having a body-facing side and a garment-facing side. The garment facing side of the absorbent core, i.e. bottom layer, is embossed to form a pattern of areas of differing density. The embossed pattern on the bottom layer of the absorbent core improves the removal of urine or other fluids from the discharge zone to be ready for the next void.

U.S. Patent Publication No. 2004/0267220 of Raymond, describes an absorbent article having an embossing pattern defined as a raised portion on an upper layer. The embossing pattern of a type letter, word, mark, hatch line, number, logo, etc, is applied. However, the embossing pattern with diamond or square edges is observed to be stiff to the wearer.

The disclosure of the aforementioned patents and publications are incorporated herein by reference thereto in their entirety.

Owing to the nature of the embossing procedure and the embossed design pattern, the absorbent core is not very smooth or comfortable when worn close to the body. If the pattern is polygonal, it makes the whole core very rigid. Sometimes the edges of the polygon also add to the discomfort of the wearer.

Furthermore because of the polygonal nature of the pattern, narrow channels are formed thereby limiting the storage capacity for the liquid that is yet to be absorbed by the core.

It is therefore desirable to have a configuration of the absorbent core that is comfortable to be worn as well as offering enhanced absorption properties.

It is an objective of the present invention to provide an improved core that is smooth to the body and comfortable to wear.

It is a further objective of the invention to provide a core with increased fluid storage and retention capacity.

It is yet another objective of the present invention to have desired rigidity in the absorbent core.

SUMMARY OF THE INVENTION

To achieve the aforementioned objectives, and to overcome the drawbacks of the prior art, the present invention provides for an absorbent core that is embossed with a circular or oval pattern. Such a configuration of an embossing pattern results in a smoother top surface as well as increased spacing between individual tufted areas, and provides more space for the body exudates to accumulate until they get absorbed by the core.

The present invention describes an absorbent article comprising a top sheet, a back sheet, an absorbent core disposed between the top sheet and the back sheet, and a fluid transfer layer disposed between the top sheet and the absorbent core. The absorbent core of the absorbent article is made of an airlaid material. Alternatively, the absorbent core may also be provided with an airlaid material having from about 45% to about 95% by weight of superabsorbent polymeric material. Further, an important aspect of the present invention is that the absorbent core is embossed, preferably with a circular pattern along its entire top surface.

The invention also includes a method of making an absorbent article that includes providing a top sheet material and a back sheet material. The method also includes preparing an absorbent core having a circular embossed pattern, and disposing the absorbent core between the top sheet material and the back sheet a material. The method further includes preparing a fluid transfer layer comprised of three dimensional aperture film, and disposing the transfer layer between the top sheet material and the absorbent core. The transfer layer can be a loft, non woven, or any other material known in the art. The core can be made of an airlaid material containing SAP.

In one embodiment, the absorbent article has a top sheet, a fluid transfer layer disposed underneath the top sheet, a back sheet, and an absorbent core disposed between the fluid transfer layer and the back sheet. The absorbent core is made of an airlaid material and can be devoid of any superabsorbent polymeric material. Further, the absorbent core is embossed with a circular pattern on its top surface. The fluid transfer layer is provided with a longitudinal length and lateral width of a smaller dimension as compared to the absorbent core. Preferably, the fluid transfer layer is a strip which does not cover the entire crotch region of the absorbent article.

In another embodiment of the present invention, the absorbent core is embossed with an oval shaped pattern.

The invented absorbent article preferably has a third insult strikethrough time of less than about 80 seconds, more preferably less than about 75 seconds, even more preferably less than about 70 seconds, and most preferably less than about 65 seconds. Further, the absorbent article preferably has a third insult rewet value of less than about 1.25 grams, more preferably less than about 1.1 grams, and most preferably less than about 1.0 grams.

DETAILED DESCRIPTION OF THE INVENTION

Figure 1:
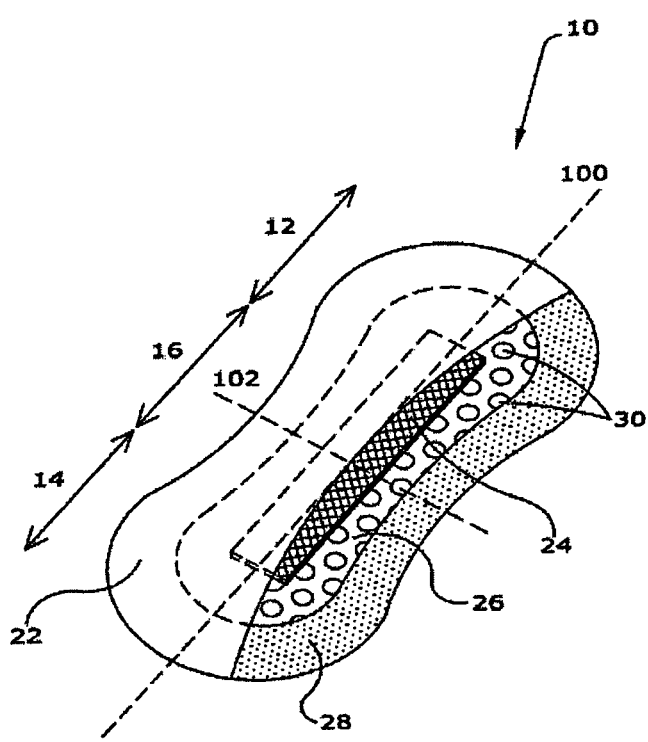
FIG. 1 shows a partially cut away top view of an absorbent article of the 30 invention.

The present invention relates to an absorbent article having improved absorbance characteristics and a method of making the same. More particularly, the present invention discloses an absorbent core of an airlaid material having a circular embossed pattern on its top surface. The present invention provides an absorbent article having superior properties of absorbency, leakage protection, and/or skin wellness, as well as being aesthetically pleasing.

As used herein, the terms "absorbent article", "absorbent garment", or simply "article" or "garment" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes pantiliners, sanitary napkins, feminine hygiene products, protective underwear, diapers, diaper covers, disposable diapers, training pants, and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent articles, without limitation, whether disposable or otherwise. The absorbent article of the present invention is optionally a pantiliner, sanitary napkin, feminine hygienic garment, protective underwear, diaper, incontinent brief, training pant, diaper holder, diaper liner, or combinations thereof. In the embodiments described herein, an exemplary structure of a pantiliner is provided. However this is not intended to limit the claimed invention. The invention will be understood to encompass, without limitation, all classes, and types of absorbent articles, including those exemplified herein.

The term "longitudinal", as used herein, refers to an axis or direction in the plane of the absorbent article that is generally aligned with a vertical plane which bisects a standing wearer into left and right body halves when the absorbent article is worn. The term "lateral" refers to the line, axis, or direction perpendicular to the longitudinal direction, which lies within the plane of the absorbent article. The length in the longitudinal axis and lateral axis represent the length and width of an absorbent article.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent article can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

The phrases "target", "target point", "target region" or "target area" are each used synonymously and refer to the area or location on an absorbent article where an insult is normally delivered by a wearer, or a nozzle or other device in an experimental method.

The term "strikethrough" is used herein to denote the amount of time it takes for a liquid to pass through the material being tested. Strikethrough is a measure of the fluid acquisition properties of the material, and can be referred to as the rate of absorbency. Strikethrough is measured in accordance with the test procedures defined hereinafter. Unless indicated otherwise, strikethrough values are reported herein in seconds.

The term "rewet" is used herein to mean the retransmission of liquid from the absorbent core to the body or wearer side of the top sheet when the disposable absorbent article is in use. Rewet therefore is a measure of the absorbent article's fluid retention capabilities under load. Low rewet means low retransmission of liquid from the fluid transport layer and/or absorbent core to the body or wearer side of the top sheet. The rewet property of an absorbent article is determined by the procedure outlined in the test procedures section below. Unless indicated otherwise, rewet values are reported herein in grams.

The present invention relates to the construction and configuration of the absorbent core that is present in absorbent articles such as diapers, training pants, sanitary pads, and pantiliners. The invention improves the absorbent core so as to make it a better absorbent article in terms of absorbent capacity as well as its feel to the portions of the body it comes in contact with. The configuration of the rest of the absorbent article, such as its shape and size, do not pertain to the invention and do not directly affect the performance of the invention. However they may be ancillary features that add to the final result of absorption capacity and feel of the core.

More particularly, the present invention relates to absorbent articles, and in particular to an absorbent article that contains a top sheet, a back sheet, an absorbent core disposed at least partially between the top sheet and the back sheet, and a fluid transfer layer disposed between the top sheet and the absorbent core. The absorbent core is comprised of an airlaid material. The airlaid material may be provided without superabsorbent polymer, or may be provided with from about 45% to about 95% by weight of superabsorbent polymer. The fluid transfer layer can be prepared with a three dimensional aperture film. The absorbent article of the invention has a third insult strikethrough time of less than about 80 seconds, and a third insult rewet value of less than about 1.25 grams.

The invention also relates in general to a method of making an absorbent article that includes providing a top sheet material and a back sheet material. The method also includes preparing an absorbent core of an airlaid material having a circular embossed pattern and disposing the absorbent core between the top sheet and the back sheet. The method further includes preparing a fluid transfer layer comprising a three dimensional aperture film, and disposing the fluid transfer layer between the top sheet and the absorbent core to form an absorbent article that has a third insult strikethrough time of less than about 80 seconds, and a third insult rewet value of less than about 1.25 grams.

The absorbent article of the invention preferably has two longitudinal edges, an anterior end and a posterior end, and two lateral edges. Those skilled in the art will recognize that "anterior" and "posterior" in the context of the invention denote for clarity purposes only the front and rear of a user, and that the absorbent article could be reversed whereby the previously described "anterior" portion becomes the "posterior" portion, and vice versa.

In the present invention, the absorbent article preferably has a third insult strikethrough of less than about 80 seconds, and a third insult rewet of less than about 1.25 grams. More preferably, the absorbent article has a third insult strikethrough of less than about 75 seconds, and a third insult rewet of less than about 1.20 grams, and even more preferably, a third insult strikethrough of less than about 70 seconds, and a third insult rewet of less than about 1.10 grams. Most preferably, the absorbent article has a third insult strikethrough of less than about 65 seconds, and a third insult rewet of less than about 1.0 grams. Although described together, the preferred absorbent articles need not have the same combination of preferred strikethrough and rewet, thus enabling an absorbent article having, say, a third insult strikethrough of less than about 75 seconds, and a third insult rewet of less than about 1.0 grams.

It is preferred in the present invention to characterize the absorbent articles by their third insult strikethrough and rewet values. This is believed to be because many materials will have comparable first insult strikethrough and rewet values, but materials that prevent leakage will be differentiated from the other materials at the second and third insult values. In addition, first insult strikethrough and rewet data do not provide much information about an absorbent article in a stressed condition. Thus, first insult strikethrough and rewet values are not necessarily good predictors of materials that will have good third insult strikethrough and rewet. In addition, it is not practical to change an absorbent article after the first insult, and in the evening, three or more insults typically occur prior to changing the absorbent article. Consequently, absorbent articles having good third insult strikethrough and rewet will be more suitable for extended use absorbent articles. Moreover, it is believed that absorbent garments that have low third insult rewet values keep the skin drier immediately after use, and since dry skin helps keep the skin healthy, consumers recognize low rewet as a benefit. Finally, it is believed that absorbent garments having low third insult strikethrough can improve the leakage performance of the absorbent article.

The present invention will now be described with reference to the accompanying drawings. The drawings are being used to illustrate the inventive concept, and do not intend to limit the invention to the embodiments shown therein.

Referring to the figures, FIG. 1 is a partially cut away depiction of an exemplary embodiment of an absorbent article 10 of the present invention as shown. The embodiment shown in FIG. 1 is a feminine hygiene product, such as a pantiliner, pad, or sanitary napkin. However, this depiction is not intended to limit the invention. The absorbent article 10 has a longitudinal axis 100 and a lateral axis 102 extending along the length and width of the absorbent article. The absorbent article 10 has a first longitudinal end 12, a second longitudinal opposed end 14, and an intermediate region 16 located between the first longitudinal end 12 and the second longitudinal end 14.

The absorbent article 10 comprises a top sheet 22, a back sheet 28, a fluid transfer layer 24 and an absorbent core 26 disposed between the top sheet 22 and the fluid transfer layer 24. When the absorbent article 10 is being worn, the top sheet 22 faces the wearer's body, and the back sheet 28 faces away from the wearer. The fluid transfer layer 24 is disposed underneath the top sheet 22. Preferably, the fluid transfer layer 24 is provided in the vicinity of the target region.

Figure 2:
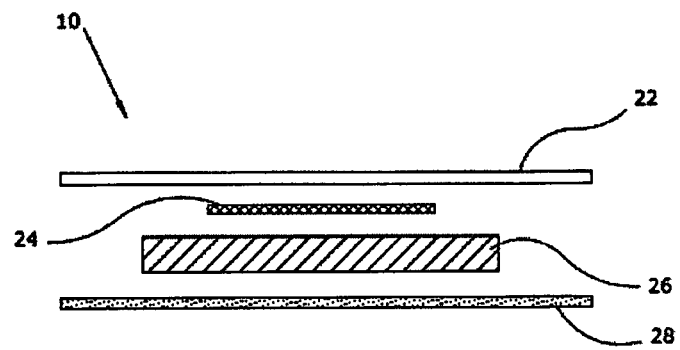
FIG. 2 is a cross sectional view of the absorbent article depicted in FIG. 1.

FIG. 2 depicts a cross sectional view of the absorbent article 10 described in FIG. 1. The absorbent article is provided with the top sheet 22, back sheet 28, absorbent core 26, and the fluid transfer layer 24. The fluid transfer layer is disposed underneath the top sheet 22, and the absorbent core 26 is disposed between at least a portion of the back sheet 28 and the fluid transfer layer 24.

The top sheet 22 and back sheet 28 may be constructed from a wide variety of materials known in the art. The invention is not intended to be limited to any specific materials for these components. The top sheet 22 and back sheet 28 can be shaped and sized according to the requirements of each of the various types of absorbent articles, or to accommodate various user sizes. In one of the configurations of the invented absorbent article, such as a pantiliner or feminine hygiene product, the top sheet 22, back sheet 28, or both, may have an oval or rectangular shape. Alternatively, in another configuration of the invented absorbent article, such as a diaper or adult incontinence brief, the top sheet 22, back sheet 28, or both may have a rectangular, trapezoidal, "T" shape, or other shape.

The moisture-pervious top sheet 22 may be made of any suitable relatively liquid-pervious material currently known in the art or later discovered that permits passage of a liquid there through. Examples of suitable top sheet materials include non-woven spun-bonded or carded webs of polypropylene, polyethylene, nylon, polyester, and blends of these materials, and the like. Non-woven materials are exemplary because such materials readily allow the passage of liquids to the underlying absorbent core 26.

The top sheet 22 preferably comprises a single-ply non-woven material that may be made of carded fibers, either adhesively or thermally bonded, spun-bonded fibers, or water entangled fibers, which generally weigh from 0.3-0.7 oz./sq. yd. (10-24 gsm), and have appropriate and effective machine direction and cross-machine (transverse) direction strength suitable for use as a top sheet material for the given application. The present invention is not intended to be limited to any particular material for the top sheet 22, and other top sheet materials will be readily apparent to those skilled in the art.

The top sheet 22 may further comprise several regions having different properties. In one embodiment of the present invention, the laterally distal portions of the top sheet 22 are preferably substantially fluid impervious and hydrophobic, while the remainder of the top sheet 22 is hydrophilic and fluid pervious. Different top sheet properties, such as fluid porosity and hydrophobicity, may be imparted upon the top sheet 22 by treating the top sheet 22 with adhesives, surfactants, or other chemicals, using a composite of different materials, or by other means. Alternatively, the different properties can be achieved by making the top sheet from three separate components, i.e. a central, fluid pervious portion, and two lateral fluid impervious portions that can also serve to form standing leg gathers. The top sheet 22 also may be treated in specific areas like the crotch region, with skin wellness ingredients like aloe and vitamin E.

The back sheet 28 generally is made of any suitable pliable liquid impervious material known in the art or later discovered. Typical back sheet materials include films of polyethylene, polypropylene, polyester, nylon, and polyvinyl chloride and blends of these materials. For example, the back sheet 28 may be made of a polyethylene film having a thickness in the range of 0.02-0.04 mm (0.8-1.2 mils). The back sheet 28 may be pigmented with, for example, titanium dioxide, calcium carbonate, and other white pigments, to provide the absorbent article 10 with a pleasing color or to render the back sheet 28 opaque enough that exudates being contained by the absorbent article 10 are not visible from outside the garment. The backsheet 28 could also be tinted with different color pigments, such as, for example, pink, blue, peach, and other colors. In addition, back sheet 28 may be formed in such a manner that it is opaque, for example, by using various inert components in the polymeric film and then biaxially stretching the film. Other back sheet materials will be readily apparent to those skilled in the art. The back sheet 28 preferably should have sufficient liquid imperviousness to prevent any leakage of fluids through the back sheet 28. The required level of liquid imperviousness may vary between different locations on the absorbent article 10.

The back sheet 28 may further comprise separate regions having different properties. In a preferred embodiment, portions of the back sheet 28 are air-permeable to improve the breathability, and therefore comfort, of the absorbent article 10. The different regions may be formed by making the back sheet 28 from a composite of different sheet materials, chemical treatment, heat treatment, or other processes or methods known in the art. Some regions of the back sheet 28 may be fluid pervious. In one embodiment of the invention, the back sheet 28 is fluid impervious in the intermediate region 16, but is fluid pervious in portions of the first and second longitudinal ends 12, 14. The back sheet 28 may also be made from a laminate of overlaid sheets of material.

In an embodiments described in FIG. 1, the top sheet 22 and back sheet 28 are substantially coterminous, or they may have different shapes and sizes. The particular design of the top sheet and back sheet may be dictated by manufacturing considerations, cost considerations, and performance considerations. Preferably, the top sheet 22 is large enough to completely cover the absorbent core 26, and the back sheet 28 is large enough to prevent leakage from the absorbent article 10. The design of top sheets 22 and back sheets 28 is known in the art, and a skilled artisan will be able to produce an appropriate top sheet 22 and an appropriate back sheet 28 without undue experimentation, using the guidelines provided herein.

The top sheet 22 and the back sheet 28 may be associated with one another using a variety of methods known in the art. For example, they may be thermally, ultrasonically, chemically, or thermal mechanically bonded to one another. They also may be joined using lines of hot melt adhesive or mechanical fasteners, such as thread, clips, or staples. In one embodiment, a hydrophilic adhesive, such as CYCLOFLEX (National Starch, Bridgewater, N.J.), is used to join the top sheet 22 to the back sheet 28. The particular joining method may be dictated by the types of materials selected for the top sheet 22 and back sheet 28.

The absorbent core 26 preferably is disposed between the top sheet 22 and the back sheet 28 in at least the crotch region 16. The absorbent core 26 may extend into either or both of the first and second longitudinal ends 12, 14. Although the absorbent core 26 depicted in FIG. 1 has a substantially oval shape, other shapes may be used, such as a "T" shape, an hourglass shape, or a rectangular shape. The shape of the absorbent core 26 may be selected to provide the greatest absorbency with a reduced amount of material. The size and capacity of the absorbent material may correspond to the desired end use of the absorbent article, for example, an incontinent brief for an adult may require a larger absorbent core than a diaper for a child. The absorbent core may be associated with the top sheet 22, back sheet 28, or any other suitable part of the absorbent article 10 by any method known in the art, in order to fix the absorbent core 26 in place.

The absorbent core 26 of the present invention is suitably constructed from an airlaid material. Various types and sources of the airlaid materials are known to a person of ordinary skill in the art. An example of the airlaid material used to prepare the absorbent core of the present invention is obtained from the EAM Company. The present invention is not restricted to a particular type of the airlaid material.

Preferably, the absorbent core 26 further comprises a super absorbent polymer distributed within the airlaid material. The types of superabsorbent materials suitable for use in the present invention are known to those skilled in the art, and may be in any operative shape, form, and size, such as particulates, fibers, particles coated with fibers or other additives, or films, for example. The superabsorbent material can be a hydrogel-forming polymeric absorbent material which may be formed from organic hydrogel-forming polymeric materials, and may include natural material such as agar, pectin, and guar gum; modified natural materials such as carboxymethyl cellulose and other biodegradable superabsorbent materials, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, polyalkylene oxide, ethylene maleic anhydride copolymers, polyvinyl ethers, polyvinyl morpholinone, polymers, and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and hydrolyzed isobutylene maleic anhydride copolymers and mixtures thereof. The hydrogel-forming polymers are preferably lightly cross linked to render the material substantially water insoluble. Cross linking may, for example, be by irradiation or covalent, ionic, Van der Waals, or hydrogen bonding. Suitable materials are available from various commercial vendors. One suitable superabsorbent material for the present invention is BASF-3900, available from BASF, a company having offices located in Ludwigshafen, Germany.

Other superabsorbent materials include multicomponent superabsorbent particulate gels. One such material is BASF E1231-99, also available from BASF. Multicomponent superabsorbent gel particles and methods to prepare them are described in the patent literature, such as, for example, U.S. Pat. Nos. 5,981,689; 6,072,101; 6,087,448; 6,121,409; 6,159,591; 6,194,631; 6,222,091; 6,235,965; 6,342,298; 6,376,072; 6,392,116; 6,509,512; and 6,555,502; U.S. Patent Publications 2001/01312; 2001/07064; 2001/29358; 2001/44612; 2002/07166; 2002/15846; and 2003/14027; and PCT Publications WO 99/25393; WO 99/25745; WO 99/25748; WO 00/56959; WO 00/63295; WO 02/10032; WO 03/18671; and WO 03/37392; the disclosures of which are incorporated herein by reference in a manner consistent with the present disclosure.

It is an important aspect of the present invention is that the absorbent core 26 is further provided with a plurality of embossing patterns on its top surface. These patterns are generally formed in curvilinear shapes. By "curvilinear" is generally meant rounded shapes devoid of any hard angles.

Embossing is performed, generally, minimally without affecting the fluff of the core. It is usually performed in lined patterns in which the embossed lines have high density and the area enclosed by these lines is slightly raised and is less dense. Usually the line pattern is chosen in such a manner so as to form an overall patterned design on the surface of the absorbent core. Embossing improves the integrity of the product.

Figure 3:
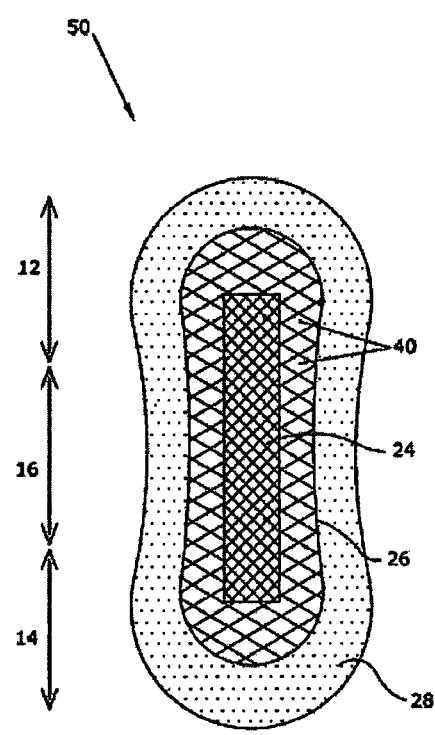
FIG. 3 shows a conventional absorbent article having a diamond-shaped embossing pattern on an absorbent core.

FIG. 3 shows an absorbent article in which an absorbent core 26 is embossed with diamond pattern 40 on its top surface. However due to the presence of edges in diamonds and other polygon shapes, such as square, rectangle and trapezoid, etc., the surface of the article is rigid and may cause discomfort to the wearer. Furthermore the high-density region formed by these lines creates a very narrow depression in which the liquid can flow and collect, until the time it is absorbed by the absorbent core.

The absorbent article according to the present invention can solve this problem by embossing the absorbent core with a shape that does not have edges and corners, such as, a circle, an oval, a clover shape, a "club" shape, an undulation, or any combination thereof. The embossing pattern in the absorbent core of the present invention is used to maintain a sufficient flexural resistance to avoid bunching of the absorbent core or formation of lumps therein when worn, or for it to be considered to be too flexible, flabby, and flimsy by consumers.

Figure 4:
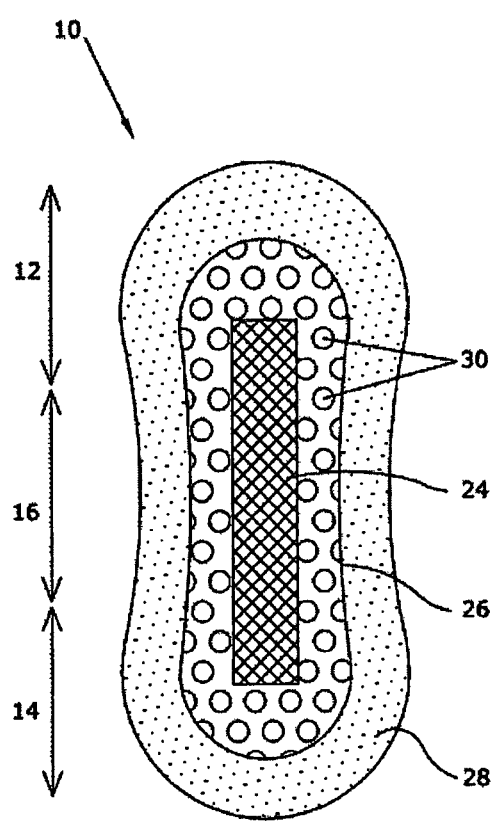
FIG. 4 shows the invented absorbent article having a circular embossing pattern on the absorbent core according to an embodiment of the invention.

Referring to FIG. 4, a top view of an embodiment of the absorbent article of the invention is shown. The absorbent article is provided with a top sheet (not shown), a back sheet 28, an absorbent core 26, and a fluid transfer layer 24. In this embodiment, a circular embossing pattern is applied on the top surface of the absorbent core 26. The circular embossing pattern 30 punched into the absorbent core 26 improves the extensibility and maintains sufficient flexural resistance of the absorbent material into the absorbent core. The circular shape allows an airlaid absorbent core to be soft and comfortable to the wearer. The circular embossing pattern is provided on the top surface of the absorbent core.

The circular pattern 30 in the absorbent core 26 may be randomly arranged or may be arranged in a regular fashion throughout the surface. The circular patterns do not intersect each other and are considerably spaced apart from each other. This forms a line, or depression, between two consecutive high density periphery sections of any two circles. These lines, or depressions, act as miniature reservoirs that hold onto the liquid, until it is absorbed by the core. The circumference of the circles and the distance between them is dictated by the desired property of softness and absorbency of the core.

Alternatively, the geometry of the embossing pattern may vary depending upon the specific desires of the wearer and the utility of the article. The embossing pattern may either extend essentially over the complete surface of the absorbent core or only selected sections thereof: for instance, the central area of the absorbent core or peripheral sections such as front and back sections and/or side sections.

Figure 5:
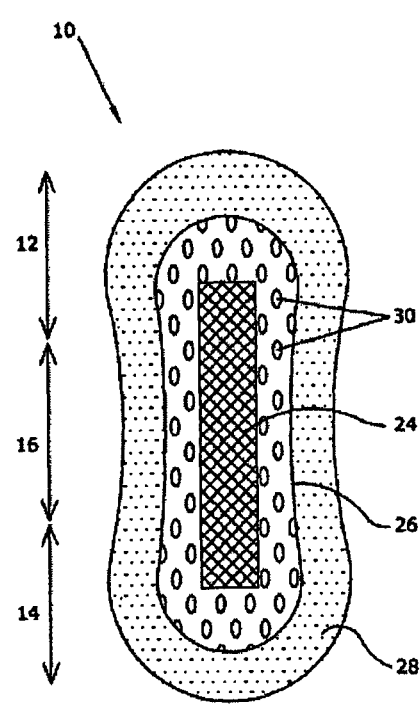
FIG. 5 shows the invented absorbent article having an oval embossing pattern on the absorbent core according to another embodiment of the invention.

The embossing pattern of a shape such as an oval, curve, undulation or any combination thereof may be used in the absorbent core 26 of the absorbent article of the invention. In another embodiment of the invention, shown in FIG. 5, the absorbent core is embossed with an oval shaped pattern. In addition, it would also be possible to have a multi-lobed embossing pattern, as long as the edges of such multi-lobed design had circular or curved edges.

Figure 6:
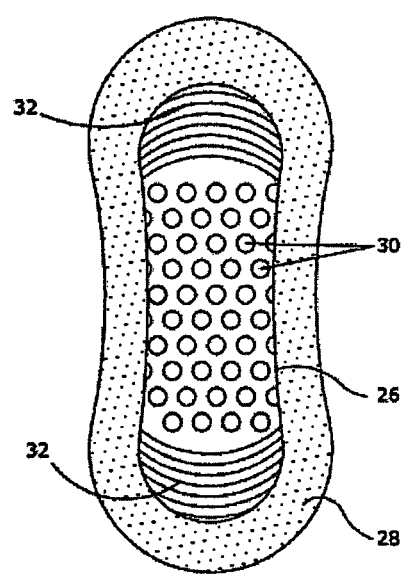
FIG. 6 shows yet another embodiment of the invented absorbent article.

The absorbent core may also be made in such a way so as to take advantage of the rigidity provided by the polygonal pattern embossing and the softness provided by curvilinear patterns. As shown in FIG. 6, the central portion of the core has a circular pattern, whereas the extremities have lines.

The embossing pattern in the absorbent core can be produced by various means known to a person of ordinary skill in the art, such as, heat or ultrasonic waves, and thermal mechanical.

The invented absorbent core may be used in one or more configurations as required when the desired absorbent article is produced. In the preferred embodiment, shown in FIG. 4, the absorbent article of the invention includes a fluid transfer layer comprised of a three dimensional aperture film. The fluid transfer layer 24 preferably is disposed between the top sheet (not shown) and the absorbent core 26. The fluid transfer layer 24 preferably extends from the first longitudinal end 12, through the intermediate region 16, and into the second longitudinal end 14, and typically corresponds substantially to the shape of the absorbent core 26. The absorbent core 26 is placed on the back sheet 28 in the crotch region of the absorbent article. The majority of the central portion of the core is covered by a three dimensional fluid transfer layer 24. On top of this layer, a top sheet (not shown) is placed. These layers are then joined together so as to form a single piece article. This joining can be by using embossing, adhesives or seams, or any other suitable means or any combination thereof.

Alternatively, the fluid transfer layer may be provided with the same longitudinal and lateral dimensions of the absorbent core, or may be provided with smaller or narrower dimensions than the absorbent core. The fluid transfer layer 24 as shown in FIGS. 1, 2, 4, and 5, has longitudinal a length and lateral width of smaller size than the respective width and length of the underlying absorbent core 26. Preferably, the fluid transfer layer 24 covers the perineum area of the absorbent core 26, and is primarily disposed, for example, in the crotch region of the absorbent article.

Figure 7:
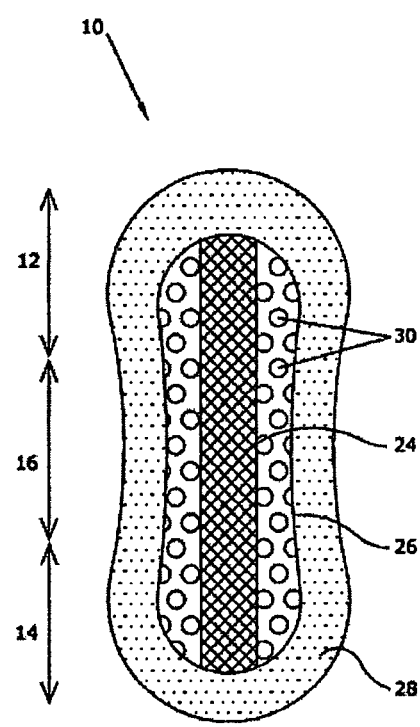
FIG. 7 shows an alternate embodiment of the invented absorbent article.

In an alternate configuration, shown in FIG. 7, the fluid transfer layer 24 may be provided with a longitudinal length which is co-terminus with the absorbent core 26 and a lateral width which is smaller as compared to the lateral width of the absorbent core.

The present invention also relates to a method of making an absorbent article that includes providing a top sheet material 22 and a back sheet material 28. The method also includes preparing an absorbent core 26 having a circular embossed pattern, and disposing the absorbent core 26 between the top sheet 22 and the back sheet 28. The method further includes preparing a fluid transfer layer 24 comprising a three dimensional aperture film, and disposing the transfer layer 24 between the top sheet 22 and the absorbent core 26. The embodiments illustrated in FIGS. 3, 5 and 7 can be prepared in accordance with the method of the invention simply by providing the fluid transfer layer 24 of different dimensions with respect to the dimension of the absorbent core 26.

The invention will be further illustrated by the following non-limiting examples.

EXAMPLE

The absorbent article of the present invention exhibits improved absorbency characteristics as demonstrated by the following Examples and Tables.

Sample Preparation: The absorbent articles were prepared for testing in accordance with the following procedures.

The absorbency characteristics, strikethrough and rewet, of the invented absorbent articles are compared with the conventional absorbent articles by using the following test procedure.

Testing Procedure

The apparatus that were used for rewet calculations included one 4"×4" Lucite cylinder block with a 1" diameter opening was used to define the area to be tested, a flat plate weighing 0.05 kilograms (4"×4"×⅛ Lucite square), a 2.2 kilogram weight, a 25 ml capacity cylinder and a top loading electronic balance, accurate ±0.01 g. In addition, we used dyed 1% saline solution (refer to STM-2000), VWR Filter paper, Grade #417, 9 cm in diameter or equivalent.

The test procedure was as follows:
1. Prepare product for testing by placing flat on a level surface.
2. Center the cylinder block on the coversheet of the product.
3. Pour measured amount of 1% saline solution into the cylinder block opening.
4. Measure saline amounts by product type:
   a. Pantyshields—2 ml;
   b. Contour Pantiliners—2 ml;
   c. Minipads—5 ml;
   d. Light Incontinent—10 ml; and
   e. All other sanitary items—10 ml.
5. Remove the cylinder block and allow product to stand for 5 minutes.
6. Weigh 10 filter papers and record weight.
7. After 5 minutes, simultaneously place the weighed filter paper, clear Lucite plate, and 2.2 kilogram weight (approx. 0.5 psi) on the center of the product. Leave in this position for 15 seconds.
8. Remove the weight and plate and weigh the filter papers.

Calculations were determined by initially weighing the filter paper in grams before and after liquid insult. In addition the average was reported.

Measuring Strikethrough and Rewet

The apparatus for determining strikethrough included a Burette clamp, 125 ml separatory funnel, Ring stand or equivalent, large beaker or bottle, at least 100 ml and a strikethrough plate (Absorbency Rate Tester) 4"×4" weight—7.8 lbs. In addition, a 1% Saline (STM 2000), a stopwatch, Ahlstrom filter papers, 2"×4" (md×cd), stanley knife or scissors and a 4.4 lb rectangular weight (2"×4"). Weight=0.5 psi.

The procedure was as follows:
1. Disassemble pad by cutting the front and back of pad.
2. Cut the pads by cutting the elastic strands (ie. Lycra) on both sides.
3. Remove top sheet and/or sublayer and replace with experimental materials.
4. Tape pad onto table with tape and stretch to make flat.
5. Place absorbency rate tester over center of product at the predicted insult area.
6. Slide separatory funnel over center of product, so that hole in strike through plate is centered under funnel tip.
7. Make sure stopcock on separatory funnel is closed and stopwatch is zeroed.
8. Dispense solution from plastic beaker on to the separatory funnel.
9. The solution amounts were as follows:

| | |
|---|---|
| a. Shields | 30 ml 1% saline solution |
| b. Guards | 30 ml 1% saline solution |
| c. Bladder Control Pads | 30 ml 1% saline solution |
| d. Light Bladder Control Pads | 10 ml 1% saline solution |

10. Open stopcock of separatory funnel, dispense the fluid into strike-through plate, and start stopwatch. Take care to always open the stopcock in the same direction.
11. Close stopcock.
12. Watch through transparent cylinder until fluid flows past strike-through plate.
13. Record result to the nearest 0.01 seconds.
14. Remove absorbency rate tester and let product sit for 10 minutes.
15. Weigh 10 filter papers and record weight on filter papers.
16. After 10 minutes, place weighed filter papers and the 2.2 lb weight in center of insult area Let weight remain for 2 minutes.
17. Remove weight and filter papers. Reweigh filter papers and subtract dry weight of filter papers to calculate rewet.
18. Repeat 5 through 17 two more times, for a total of three insults.

The calculations were conducted by weighing the filter paper before an after insult in grams. Absorbency rate was measured in seconds (sec) and Rewet value in grams (g).

The experimental protocol for measuring strikethrough and rewet properties are known to a person of ordinary skill in the art and has been additionally described in various patent publications, such as, U.S. Pat. No. 6,852,905 and U.S. Pat. No. 6,610,391, the pertinent disclosures of which are incorporated by reference herein.

Table 1 below summarizes the results obtained through above test procedures on several examples of the article of the present invention and control absorbent articles.

TABLE 1

|  |  | Dry Pr. Wt. (gm) | Wet Pr. Wt. (gm) | Total Capa (gm) | Thickness (mm) Middle | Strikethrough | | | Rewet | | |
|---|---|---|---|---|---|---|---|---|---|---|---|
|  |  |  |  |  |  | 1$^{st}$ Rate (sec) | 2$^{nd}$ Rate (sec) | 3$^{rd}$ Rate (sec) | 1$^{st}$ Rewet | 2$^{nd}$ Rewet | 3$^{rd}$ Rewet |
| Control diamond embossing | 1 | 4.30 |  |  | 2.48 | 37.06 | 69.13 | 100.88 | 0.04 | 0.06 | 0.36 |
|  | 2 | 4.30 |  |  | 2.48 | 33.66 | 55.25 | 78.68 | 0.04 | 0.05 | 0.31 |
|  | 3 | 4.19 |  |  | 2.50 | 31.37 | 54.53 | 92.32 | 0.05 | 0.06 | 0.17 |
|  | 4 | 4.25 |  |  | 2.46 | 35.09 | 63.66 | 84.69 | 0.04 | 0.06 | 0.56 |
|  | 5 | 4.41 |  |  | 2.50 | 34.75 | 55.78 | 73.62 | 0.06 | 0.05 | 0.16 |
|  | Avg. | 4.29 |  |  | 2.48 | 34.39 | 59.67 | 86.04 | 0.05 | 0.06 | 0.31 |
|  | Std | 0.08 |  |  | 0.02 | 2.09 | 6.45 | 10.84 | 0.01 | 0.01 | 0.16 |
| Invented circular embossing | 1 | 4.58 |  |  | 2.44 | 27.08 | 48.43 | 72.37 | 0.06 | 0.06 | 1.83 |
|  | 2 | 4.49 |  |  | 2.40 | 30.53 | 47.31 | 72.75 | 0.04 | 0.07 | 2.25 |
|  | 3 | 4.57 |  |  | 2.46 | 32.25 | 52.71 | 80.15 | 0.05 | 0.11 | 3.24 |
|  | 4 | 4.50 |  |  | 2.43 | 33.65 | 53.92 | 90.85 | 0.04 | 0.12 | 2.72 |
|  | 5 | 4.56 |  |  | 2.44 | 30.32 | 49.97 | 70.65 | 0.04 | 0.08 | 2.23 |
|  | Avg. | 4.54 |  |  | 2.43 | 30.99 | 50.43 | 80.96 | 0.05 | 0.09 | 2.45 |
|  | Std | 0.04 |  |  | 0.03 | 2.65 | 2.77 | 9.13 | 0.01 | 0.03 | 0.54 |

Various other embodiments are possible within the spirit of the invention, and the aforementioned examples and embodiments are simply meant to be for explanatory purposes, and are not intended to limit the invention in any manner. The articles of the invention may be made from various kinds of materials available in the field and known to a person skilled in the art. The embossing may be done using various techniques prevalent in the field. The invention intends to cover all the equivalent embodiments and is limited only by the appended claims.

What is claimed is:

1. An absorbent article having a third insult strikethrough time of less than 80 seconds and a third insult rewet value of less than 2.5 grams, said absorbent article comprising:
   a top sheet;
   a fluid transfer layer, said fluid transfer layer being disposed beneath said top sheet;
   a back sheet; and
   an absorbent core disposed between said fluid transfer layer and said back sheet, the absorbent core comprising a top surface facing the fluid transfer layer, the top surface defining the perimeter of the absorbent core, said absorbent core comprising an airlaid material, wherein said absorbent core is embossed with a closed curvilinear pattern that repeats over the entire top surface area of the absorbent core and is at least one of a hollow circle, an oval or a clover shape, and the closed curvilinear pattern is randomly embossed on the top surface area of the absorbent core.

2. The absorbent article as claimed in claim 1, wherein said absorbent core further comprises a super absorbent polymeric material.

3. The absorbent article as claimed in claim 2, wherein said absorbent core comprises from 45% to 95% by weight of super absorbent polymeric material.

4. The absorbent article as claimed in claim 1, wherein said fluid transfer layer is a three dimensional aperture film.

5. The absorbent article as claimed in claim 1, wherein said third insult strikethrough time is less than 75 seconds.

6. The absorbent article as claimed in claim 5, wherein said third insult strikethrough time is less than 65 seconds.

7. The absorbent article as claimed in claim 1, wherein said third insult rewet value is less than 1.10 grams.

8. The absorbent article as claimed in claim 7, wherein said third insult rewet value is less than 1.0 grams.

9. The absorbent article as claimed in claim 1, wherein said embossing is performed by heated rollers and ultrasonic bonding.

10. A method for preparing an absorbent article having a third insult strikethrough time of less than 80 seconds and a third insult rewet value of less than 2.5 grams, said method comprising the step of:
    preparing a top sheet;
    preparing a fluid transfer layer;
    disposing said fluid transfer layer beneath said top sheet;
    preparing a back sheet;
    preparing an absorbent core comprising an airlaid material, the absorbent core comprising a top surface facing the fluid transfer layer, the top surface defining the perimeter of the absorbent core;
    embossing said absorbent core with a closed curvilinear pattern that repeats over the entire top surface of the absorbent core and that is at least one of a hollow circle, an oval or a clover shape, the closed curvilinear pattern being randomly embossed on the top surface area of the absorbent core; and
    disposing said absorbent core between said fluid transfer layer and said back sheet.

11. The method as claimed in claim 10, wherein said absorbent core further comprises super absorbent polymeric material.

12. The method as claimed in claim 11, wherein said absorbent core comprises 5 from 45% to 95% by weight of super absorbent polymeric material.

13. The method as claimed in claim 10, wherein said fluid transfer layer is a three dimensional aperture film.

14. The method as claimed in claim 10, wherein said third insult strikethrough time is less than 75 seconds.

15. The method as claimed in claim 14, wherein said third insult strikethrough time is less than 65 seconds.

16. The method as claimed in claim 10, wherein said third insult rewet value is less than 1.10 grams.

17. The method as claimed in claim 16, wherein said third insult rewet value is less than 1.0 grams.

18. The method as claimed in claim 10, wherein said embossing is performed by means including heated rollers and ultrasonic bonding.

19. An absorbent article having a third insult strikethrough time of less than 80 seconds and a third insult rewet value of less than 2.5 grams, said absorbent article comprising:
    a top sheet;

a fluid transfer layer, said fluid transfer layer being disposed beneath said top sheet;

a back sheet; and an absorbent core disposed between said fluid transfer layer and said back sheet, the absorbent core comprising a top surface facing the fluid transfer layer, the top surface defining the perimeter of the absorbent core, said absorbent core comprising an airlaid material, wherein said absorbent core is embossed with a pattern that repeats over the entire top surface of the absorbent core and the pattern is club shape.

20. A method for preparing an absorbent article having a third insult strikethrough time of less than 80 seconds and a third insult rewet value of less than 2.5 grams, said method comprising the step of:

preparing a top sheet;

preparing a fluid transfer layer;

disposing said fluid transfer layer beneath said top sheet;

preparing a back sheet;

preparing an absorbent core comprising an airlaid material, the absorbent core comprising a top surface facing the fluid transfer layer, the top surface defining the perimeter of the absorbent core;

embossing said absorbent core with a pattern that repeats over the entire top surface of the absorbent core, the pattern being a club shape; and disposing said absorbent core between said fluid transfer layer and said back sheet.

* * * * *